(12) United States Patent
Tybinkowski et al.

(10) Patent No.: US 11,547,376 B2
(45) Date of Patent: Jan. 10, 2023

(54) DEPLOYABLE STABILIZATION FEET FOR A PORTABLE MEDICAL IMAGING SYSTEM

(71) Applicant: Dedicated2Imaging, LLC, Portsmouth, NH (US)

(72) Inventors: Andrew Tybinkowski, Topsfield, MA (US); Eric M. Bailey, North Hampton, NH (US); Jamie Brooks, Amesbury, MA (US)

(73) Assignee: Dedicated2Imaging, LLC., Portsmouth, NH (US)

( * ) Notice: Subject to any disclaimer, the term of this patent is extended or adjusted under 35 U.S.C. 154(b) by 338 days.

(21) Appl. No.: 17/014,108

(22) Filed: Sep. 8, 2020

(65) Prior Publication Data
US 2021/0106297 A1    Apr. 15, 2021

Related U.S. Application Data

(60) Provisional application No. 62/913,359, filed on Oct. 10, 2019.

(51) Int. Cl.
*A61B 6/00* (2006.01)

(52) U.S. Cl.
CPC ............ *A61B 6/4405* (2013.01); *A61B 6/447* (2013.01); *A61B 6/4476* (2013.01); *A61B 2560/02* (2013.01); *A61B 2560/04* (2013.01)

(58) Field of Classification Search
CPC . A61B 2560/02; A61B 2560/04; A61B 6/035; A61B 6/4405; A61B 6/447; A61B 6/4476; A61G 7/08
See application file for complete search history.

(56) References Cited

U.S. PATENT DOCUMENTS

| | | |
|---|---|---|
| 4,061,309 A | 12/1977 | Hanser |
| 4,082,249 A | 4/1978 | Valdespino et al. |
| 5,176,391 A | 1/1993 | Schneider et al. |
| 5,628,521 A | 5/1997 | Schneider et al. |
| 5,799,054 A | 8/1998 | Hum et al. |
| 5,878,355 A | 3/1999 | Berg et al. |

(Continued)

FOREIGN PATENT DOCUMENTS

| | | |
|---|---|---|
| CN | 2352433 Y | 12/1999 |
| CN | 203513184 U | 4/2014 |

(Continued)

*Primary Examiner* — Dani Fox

(57) ABSTRACT

A hydraulic stabilizer system for a portable medical imaging system. The system includes at least two hydraulic cylinders each having a shaft extending through a first wall of the respective cylinder, wherein each shaft is moveable relative to the respective cylinder. First and second ends of each shaft include a spring support element and a foot for contacting associated uneven floor portions. A retraction spring is located between the spring support element and an inner surface of the first wall of each cylinder. The system also includes a hydraulic circuit for supplying hydraulic fluid to the cylinders, wherein the cylinders are in fluid communication with each other. Hydraulic fluid is pumped into the cylinders to cause downward movement of the shafts until the feet contact the associated uneven floor portions such that the pressure exerted by the feet against the associated uneven floor portions is equalized.

20 Claims, 7 Drawing Sheets

(56) References Cited

U.S. PATENT DOCUMENTS

| | | |
|---|---|---|
| 2014/0343570 A1 | 11/2014 | Schena et al. |
| 2015/0223891 A1 | 8/2015 | Miller et al. |
| 2015/0223892 A1 | 8/2015 | Miller et al. |
| 2015/0227127 A1 | 8/2015 | Miller et al. |
| 2017/0065354 A1 | 3/2017 | Shiels et al. |
| 2017/0065355 A1* | 3/2017 | Ross .................. A61B 34/30 |
| 2017/0066003 A1 | 3/2017 | Baumgartner et al. |
| 2017/0087730 A1 | 3/2017 | Robinson et al. |
| 2018/0085480 A1 | 3/2018 | Mauzerall et al. |
| 2018/0346008 A1* | 12/2018 | Nahum .................. B62B 5/049 |
| 2019/0145471 A1 | 5/2019 | Carbone et al. |
| 2019/0216555 A1 | 7/2019 | DiMaio et al. |

FOREIGN PATENT DOCUMENTS

| | | |
|---|---|---|
| CN | 203513186 U | 4/2014 |
| CN | 103863050 A | 6/2014 |
| CN | 208007141 U | 10/2018 |
| EP | 0297138 A1 | 1/1989 |
| GB | 1315833 A | 5/1973 |
| WO | 2017180566 A2 | 10/2017 |

\* cited by examiner

DEPLOYABLE STABILIZATION FEET FOR A PORTABLE MEDICAL IMAGING SYSTEM

PRIORITY CLAIM

This application claims the benefit under 35 U.S.C. § 119(e) of U.S. Provisional Application No. 62/913,359 filed on Oct. 10, 2019 and entitled DEPLOYABLE STABILIZATION FEET FOR A PORTABLE MEDICAL IMAGING SYSTEM, which is incorporated herein by reference in its entirety and to which this application claims the benefit of priority.

TECHNICAL FIELD

Aspects of the present invention relate to a hydraulic stabilizer system for a portable medical imaging system, and more particularly, to a hydraulic stabilizer system having at least two hydraulic cylinders each having a shaft wherein each shaft includes a foot for contacting associated uneven floor portions wherein the cylinders are in fluid communication with each other such that when hydraulic fluid is pumped into the cylinders the shafts move downward until the feet contact the associated uneven floor portions such that the pressure exerted by the feet against the associated uneven floor portions is equalized.

BACKGROUND

Portable medical imaging systems, such as portable computed tomography (CT) imaging systems, are being increasingly utilized by medical personnel. Portable imaging systems are frequently transported using carts or trolleys that include motorized wheels for facilitating movement of the imaging system from one location to another. It is desirable to provide a portable imaging system having relatively fast scan times while also providing improved spatial resolution in an image. However, a wobbling movement is frequently generated during operation of such portable imaging systems, resulting in substantial blurring of the spatial resolution in an image generated by the system. This is exacerbated by relatively high rotation and translation speeds of imaging equipment and uneven flooring upon which the imaging system is located. For example, many CT scanners generate a slice thickness (i.e. resolution) as thin as approximately 0.5 mm. A portable imaging system that wobbles at a magnitude of approximately 3 mm generates "wobbling forces" that substantially degrade this level of resolution. The wobbling forces increase by the square of velocity. Thus, an imaging system that operates at 60 rpm, for example, will have 4 times (2 squared) the forces than an imaging system operating at 30 rpm.

In order to minimize image degradation, many conventional portable imaging systems are designed such that they generate relatively small wobbling forces. A method of achieving small wobbling forces includes using lower rotational and/or translation speeds. However, this compromises scanner performance since the length of time needed to perform a scan is increased and image quality is more likely to be affected by patient and/or organ movement. Another method is to provide improved rotational balancing, both static, and more importantly dynamic, to reduce wobbling forces. However, this is difficult to achieve in compact portable imaging systems and the difficulty increases with increased operational speeds.

SUMMARY OF THE INVENTION

A hydraulic stabilizer system for a portable medical imaging system is disclosed. The system includes at least two hydraulic cylinders each having a shaft extending through a first wall of the respective cylinder, wherein each shaft is moveable relative to the respective cylinder. A second end of each shaft includes a foot for contacting associated uneven floor portions and a first end of each shaft includes a spring support element. A retraction spring is located between the spring support element and an inner surface of the first wall of each cylinder. The system also includes a hydraulic circuit for supplying hydraulic fluid to the cylinders, wherein the cylinders are in fluid communication with each other. Hydraulic fluid is pumped into the cylinders to cause downward movement of the shafts until the feet contact the associated uneven floor portions such that the pressure exerted by the feet against the associated uneven floor portions is equalized.

Those skilled in the art may apply the respective features of the present invention jointly or severally in any combination or sub-combination.

BRIEF DESCRIPTION OF THE DRAWINGS

The exemplary embodiments of the invention are further described in the following detailed description in conjunction with the accompanying drawings, in which.

To facilitate understanding, identical reference numerals have been used, where possible, to designate identical elements that are common to the figures. The figures are not drawn to scale.

DETAILED DESCRIPTION

Figure 1:
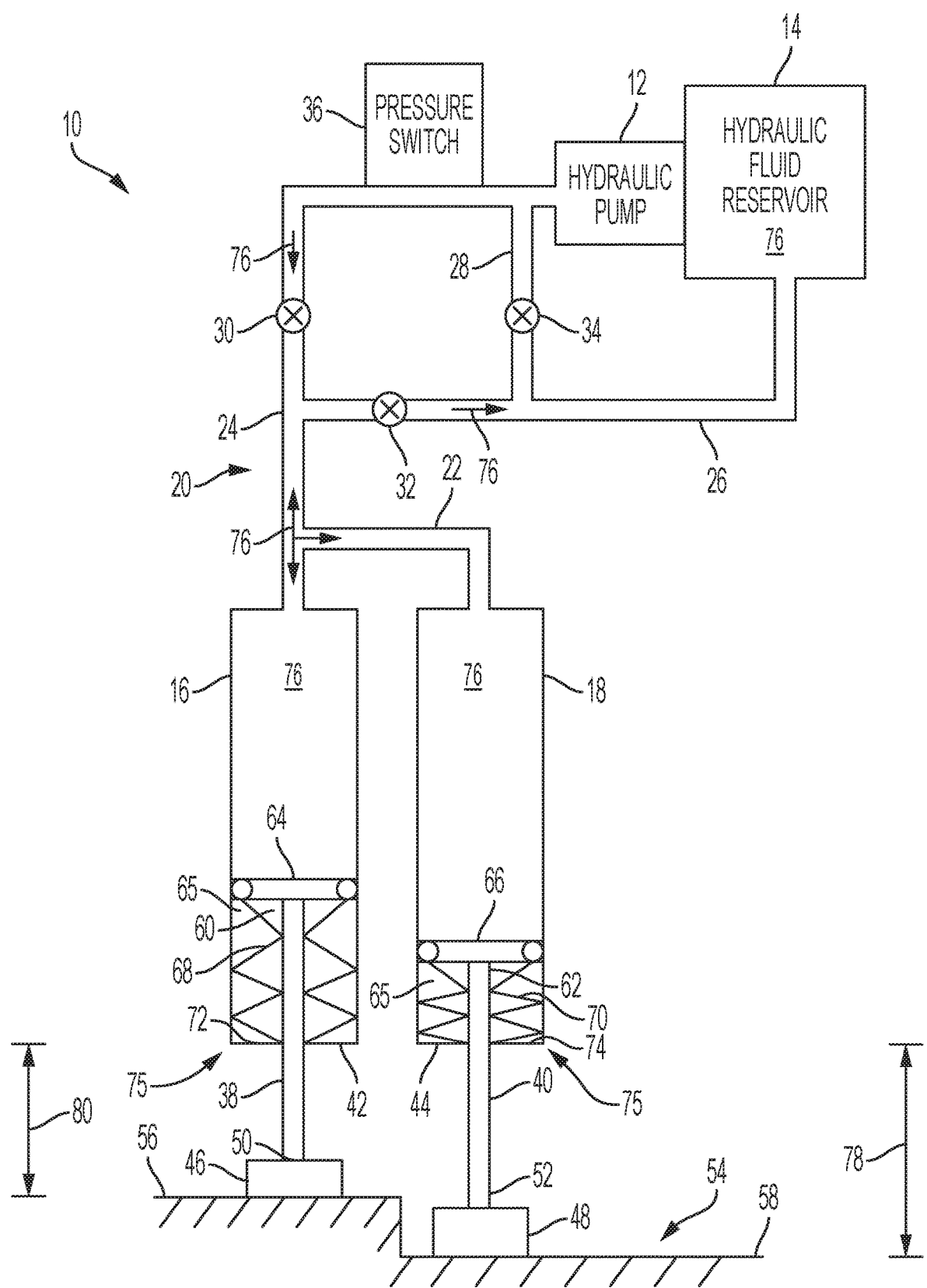
FIG. 1 depicts a hydraulic stabilizer system for deploying at least one foot for stabilizing a portable medical imaging system.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

A portable medical imaging system is frequently transported in a medical facility using a cart or trolley that includes wheels for facilitating movement of the imaging system. The floors of the medical facility may be fabricated from various materials and have varying levels of quality and flatness. In addition, the trolley encounters items such as door jambs and elevator thresholds when the imaging system is moved from one location to another that subject the imaging system to bumps and physical shocks. The trolley wheels are equipped with shock absorbing elements to damp movement of the trolley caused by the bumps and shocks. However, the shock absorbing elements create a base for an imaging scanner that is not sufficiently stable for generating sub-millimeter images of sufficient resolution when using, for example, a computed tomography (CT) gantry operating at 60 rpm and translating at 35 mm per second.

In accordance with an aspect of the invention, at least one deployable foot is used to stabilize a portable imaging system subjected to wobbling forces. Referring to FIG. 1, a hydraulic stabilizer system 10 for deploying at least one foot for stabilizing a portable medical imaging system 82 (see FIG. 2) is shown. For purposes of illustration, the invention will be described with reference to two feet as shown in FIG. 1. The stabilizer system 10 includes a hydraulic pump 12, a hydraulic fluid reservoir 14, first 16 and second 18 hydraulic cylinders and a hydraulic circuit 20 having first 22, second 24, third 26 and fourth 28 circuit portions. The first 16 and second 18 cylinders are in fluid communication with each other via the first circuit portion 22. The pump 12 is in fluid communication with the first circuit portion 22 via the second circuit portion 24. The fluid reservoir 14 is in fluid communication with the second circuit portion 24 via the third circuit portion 26. The fourth circuit portion 28 is in fluid communication with the second 24 and third 26 circuit portions. Thus, the pump 12 and fluid reservoir 14 are in fluid communication with the first 16 and second 18 cylinders and the first 16 and second 18 cylinders are in fluid communication with each other. In addition, the second 24, third 26 and fourth 28 circuit portions include extend 30, retract 32 and pressure relief 34 valves, respectively. The second circuit portion 24 also includes a pressure switch 36 located between the pump 12 and the extend valve 30.

The first 16 and second 18 cylinders include first 38 and second 40 vertically moveable shafts that extend through first 42 and second 44 bottom walls of the first 16 and second 18 cylinders, respectively. First 46 and second 48 stabilizing feet are attached to first 50 and second 52 bottom ends of the first 38 and second 40 shafts, respectively. Thus, the first 46 and second 48 feet are independently moveable relative to each other. FIG. 1 depicts an uneven floor 54 having an uneven floor location wherein a first floor portion 56 of the floor 54 underneath the first foot 46 is vertically higher than a second floor portion 58 of the floor 54 underneath the second foot 48. In accordance with an aspect of the invention, the first 46 and second 48 feet are independently moveable in order to contact the first 56 and second 58 floor portions, respectively, and thus are able to adjust to different floor heights in order to stabilize the portable imaging system 82. Each foot 46, 48 is shaped to provide sufficient friction with the floor 54 and is fabricated from a suitable material that provides sufficient friction while at the same time does not mar or damage the floor 54.

First 60 and second 62 top ends of the first 38 and second 40 shafts include first 64 and second 66 spring support elements, respectively. First 68 and second 70 retraction spring elements are located between the first 64 and second 66 supports and first 72 and second 74 inner surfaces of the first 42 and second 44 bottom walls, respectively. Downward movement of the first 64 and second 66 supports causes contact between top portions 65 of the first 68 and second 70 springs and the first 64 and second 66 supports. This compresses the first 68 and second 70 springs due to contact between bottom portions 75 of the first 68 and second 70 springs and the first 72 and second 74 inner surfaces, respectively. Referring to FIG. 1, the second spring 70 is shown compressed more than the first spring 68 due to the uneven floor 54. The first 68 and second 70 springs are configured to oppose compression. When compressed, the first 68 and second 70 springs provide sufficient bias to retract the first 46 and second 48 feet as will be described.

In order to deploy the first 46 and second 48 feet, the extend valve 30 is opened and the retract valve 32 is closed. Hydraulic fluid 76 from the fluid reservoir 12 is then pumped by the pump 12 into the first 16 and second 18 cylinders, which are in fluid communication with each other via the first circuit portion 22 as previously described, until a predetermined pressure is detected by the pressure switch 36. Hydraulic pressure against the first 64 and second 66 supports, due to the hydraulic fluid 76, causes downward movement of the first 64 and second 66 supports, thus compressing the first 68 and second 70 springs, respectively. This in turn causes downward movement of the first 46 and second 48 feet until the first 46 and second 48 feet contact the first 56 and second 58 floor portions, respectively. In particular, a second stroke length 78 that the second foot 48 travels is greater than a stroke length 80 that the first foot 46 travels, thus compensating for the uneven floor 54. When this occurs, the pressure that the first 46 and second 48 feet exert against the first 56 and second 58 floor portions is equalized. In an aspect of the invention, the pressure level is selected such that the first 46 and second 48 feet stabilize the portable imaging system 82 without completely supporting the weight of the portable imaging system 82. In accordance with another aspect of the invention, the first 46 and second 48 feet stabilize the portable imaging system 82 when the system 82 is subjected to wobbling forces thus enabling the use of relatively high rotation and translation speeds which in turn enable the generation of images having sufficient spatial resolution. Alternatively, the pressure level is selected such that the first 46 and second 48 feet are able to support the entire weight of the portable imaging system 82 with or without the assistance of trolley wheels. The pressure relief valve 34 serves to limit the hydraulic pressure in the stabilizer system 10 to prevent over-pressurization due to equipment or logic failure.

Once the feet 46, 48 are deployed, the extend valve 30 is closed thus maintaining hydraulic pressure in the first 16 and second 18 cylinders. The pump 12 is subsequently turned off. The portable imaging system 82 is then operated to generate a desired scan of a patient. When the scan is complete, the retract valve 32 is opened to relieve the hydraulic pressure in the first 16 and second 18 cylinders at a predetermined rate. This causes the first 68 and second 70 springs to expand and which in turn causes upward movement of the first 64 and second 66 supports. The first 46 and second 48 feet then move upwards or retract into a retracted position wherein the first 46 and second 48 feet are not in contact with the first 56 and second 58 floor portions. Hydraulic fluid 76 from the first 16 and second 18 cylinders flows into the fluid reservoir 14 when the retract valve 32 is opened. In accordance with an aspect of the invention, the first 68 and second 70 springs and a retract valve orifice are designed to provide a relatively slow and steady retraction of the first 46 and second 48 feet.

Figure 2:
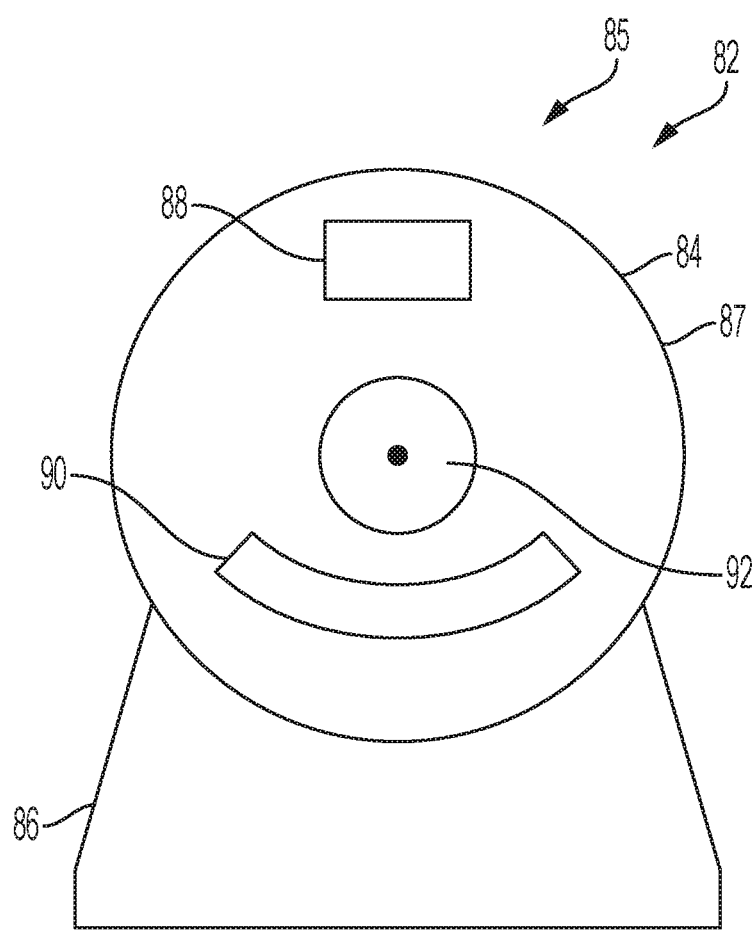
FIG. 2 depicts a portable medical imaging system in accordance with an aspect of the invention.

Referring to FIG. 2, a portable medical imaging system 82 in accordance with an aspect of the invention is shown. The portable imaging system 82 is transported using a trolley 94 (see FIGS. 3A-3D) that includes trolley wheels 98, 102 for facilitating movement of the imaging system from one location to another in a medical facility. The portable imaging system 82 may have an imaging gantry 84 that is moveable relative to a patient and a stationary gantry base 86. The portable imaging system 82 may be a computed tomography (CT) system 85 having a CT gantry 87, X-ray generator 88, X-ray detector assembly 90 and a center opening 92 for receiving a patient or a part of a patient's anatomy to be scanned such as the head. The portable imaging system 82 further includes various electronic hardware and software for controlling the apparatus and processing the acquired data so as to generate CT scans. Alternatively, the portable imaging system 82 may be a magnetic resonance imaging (MRI), positron emission tomography (PET), single-photon emission computerized tomography (SPECT), X-ray, PET/CT or SPECT/CT imaging system or use surgery (i.e. surgical C-arm) or interventional technologies. In an embodiment, the portable imaging system 82 may include an electronic board that controls pump motor power as well as control switches. The board may also include a display for displaying the output of the pressure switch 36.

Figure 3A:
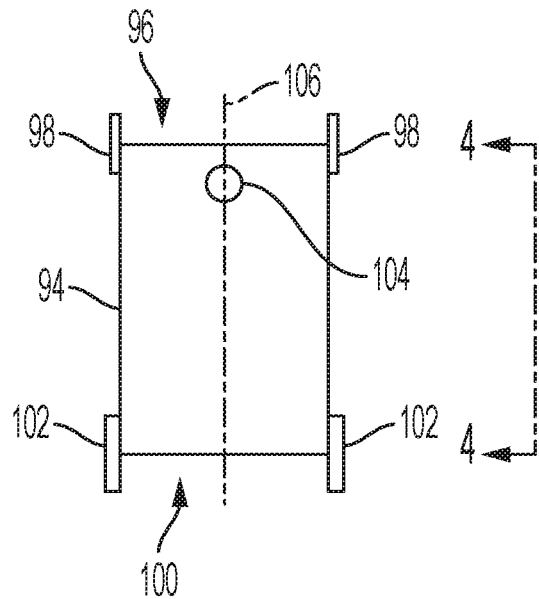
FIGS. 3A-3D show bottom views of a trolley for transporting the portable medical imaging system and depicts alternate arrangements for stabilizing feet.
Figure 3B:
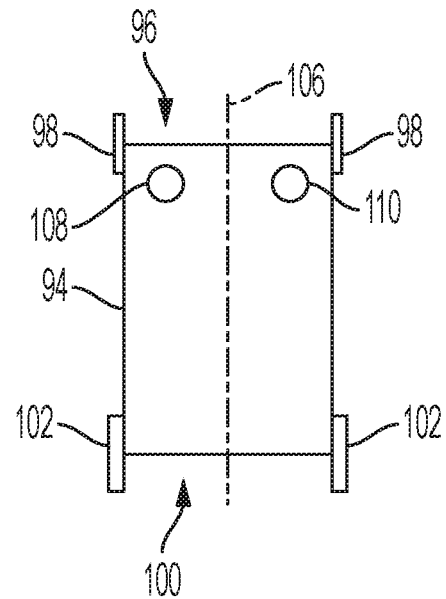
Figure 3C:
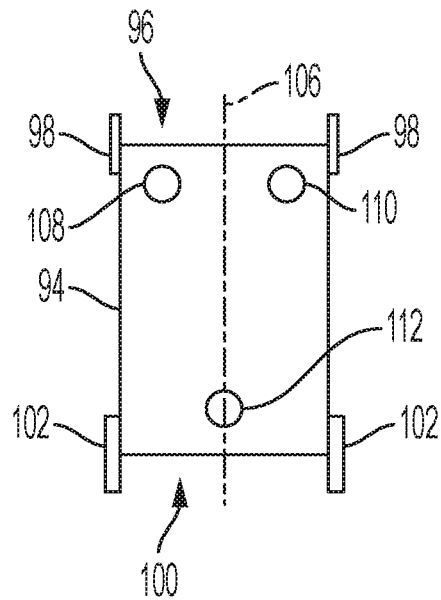
Figure 3D:
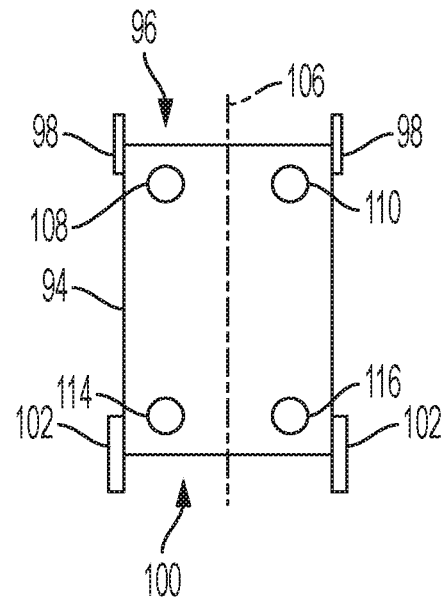

FIGS. 3A-3D show bottom views of a trolley 94 for transporting the portable medical imaging system 82 and depicts alternate arrangements for stabilizing feet. The trolley 94 may have a substantially rectangular shape having a front end 96 that includes front trolley wheels 98 and a rear end 100 that includes rear trolley wheels 102 generally located adjacent corners of the trolley 94. Alternatively, the trolley 94 may have a substantially square shape or other suitable shape. The wheels 98, 102 enable movement of the trolley 94 along a center longitudinal axis 106. In addition, one or more of the wheels 98, 102 may be motor driven. In FIG. 3A, a single front stabilizing foot 104 is located on a center axis 106 of the trolley 94 and near the front end 96. In FIG. 3B, the trolley 94 includes first 108 and second 110 stabilizing feet located near the front end 96. In FIG. 3C, the trolley 94 includes the first 108 and second 110 stabilizing feet located near the front end 96 and a single rear stabilizing foot 112 located near the rear end 100 and on the center axis 106. In FIG. 3D, the trolley 94 includes the first 108 and second 110 stabilizing feet located near the front end 96 and third 114 and fourth 116 stabilizing feet located near the rear end 100. The stabilizing feet 104, 108, 110, 112, 114, 116 each extend from a hydraulic cylinder 16, 18 and are moveable due to hydraulic pressure to a deployed position wherein the stabilizing feet 104, 108, 110, 112, 114, 116 contact the floor 54 to stabilize the portable imaging system 82 as previously described in relation to FIG. 1.

Referring to Table 1, the advantages and disadvantages with respect to using 1-4 stabilizing feet for the trolley 94 are shown.

TABLE 1

| Number of Stabilizing Feet | Advantage | Disadvantage |
| --- | --- | --- |
| 1 | Lowest cost/complexity | Single foot is subjected to most pressure. |
| 2 | Moderate complexity | Rear wheel support still needed. |
| 3 | Additional foot results in less force per foot | Third foot is still subjected to relatively large pressure. |
| 4 | Lowest force per foot. No wheels needed for support during scanning. | Most complex. Difficult to level. Relatively high cost. |

It understood that more than four stabilization feet may be used to stabilize the trolley 94. Further, the position of the stabilizing feet 104, 108, 110, 112, 114, 116 relative to the front wheels 98 and rear wheels 102 and/or front 96 and rear 100 ends may be adjustable in trolley 94 to accommodate a specific uneven floor location or a floor 54 having more than one uneven floor location to provide an asymmetric or offset arrangement of stabilizing feet 104, 108, 110, 112, 114, 116 relative to the center axis 106.

In accordance with an aspect of the invention, the trolley 94 includes the first 108 and second 110 stabilization feet located near the front end 96 that provide stabilization for the portable imaging system 82 as previously described in relation to FIGS. 1 and 3B wherein the rear wheels 102 are motorized and the front wheels 98 are caster wheels. The first 108 and second 110 stabilization feet and the rear wheels 102 form a stable plane for supporting the portable imaging system 82.

As previously described, the first 108 and second 110 stabilization feet are moved by hydraulic fluid 76 pumped into first 16 and second 18 cylinders, respectively, that are in fluid communication with each other via the first circuit portion 22. Each foot 108, 110 then travels a sufficient distance downward to make contact with a respective portion of the floor 54 (i.e. each foot travels a different distance depending on floor flatness). When this occurs, the pressure that the first 108 and second 110 stabilization feet exert against the first 56 and second 58 floor portions is equalized.

Alternatively, electric actuators may be used to deploy the feet. In arrangements utilizing more than one foot, sensors are utilized to control the length of deployment of each foot (i.e. stroke length) depending on the degree of unevenness of the floor.

In an aspect of the invention, a plurality of the wheels 98, 102 may be omnidirectional wheels, mecanum wheels or the like to enable movement of the trolley 94 in directions other than along the longitudinal axis 106. In another embodiment, the trolley 94 may include a fifth stabilizing foot located on an axis of the trolley 94 that is orthogonal to the longitudinal axis 106. In this embodiment, the fifth stabilizing foot is used in conjunction with either the first 108 and third 114 stabilizing feet or the second 110 and fourth 116 stabilizing feet to stabilize the trolley 94 and thus the portable imaging system 82 about the orthogonal axis.

Figure 4A:
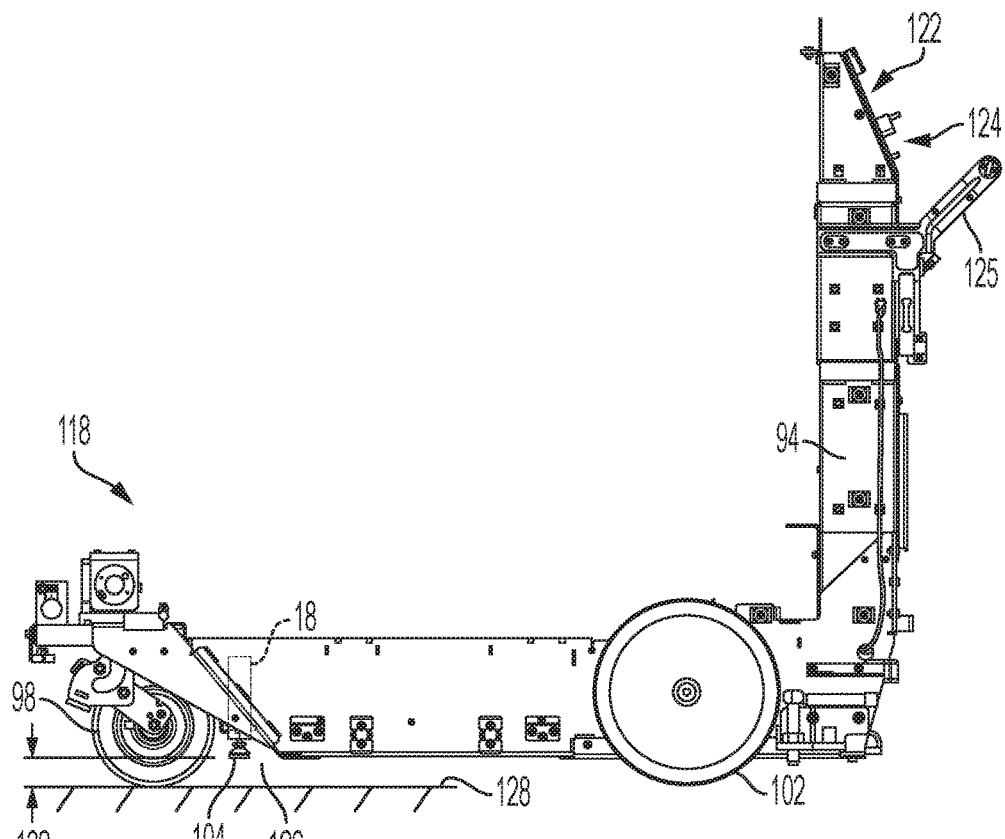
FIGS. 4A-4C depict side views of the trolley.
Figure 4B:
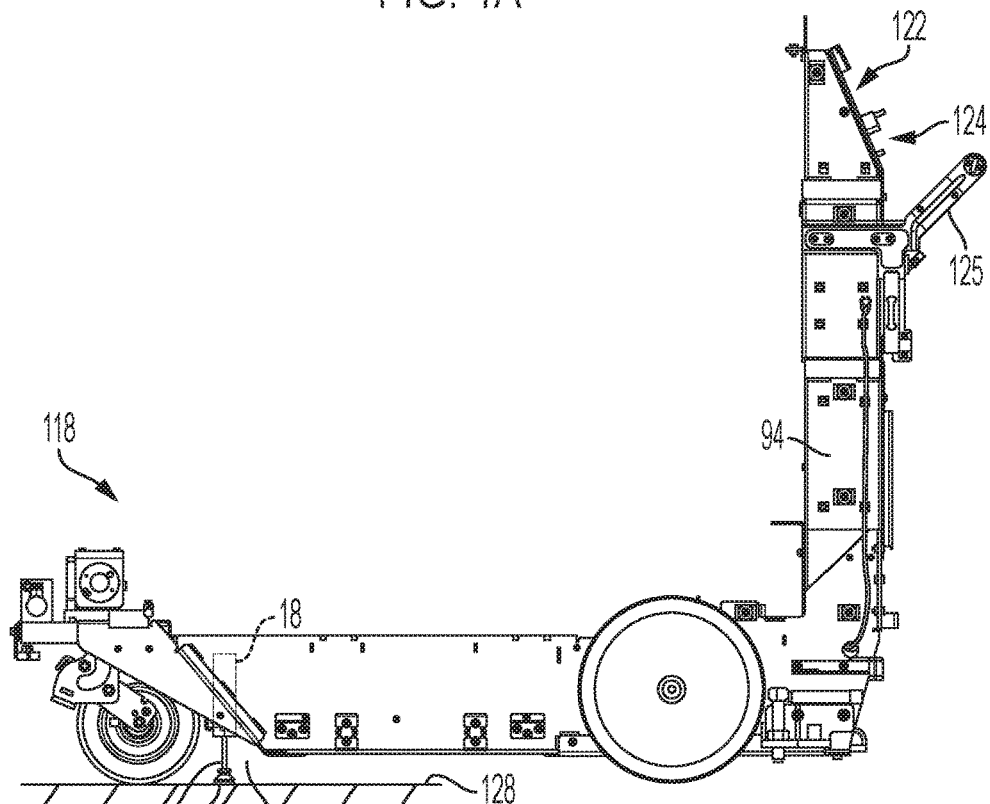
Figure 4C:
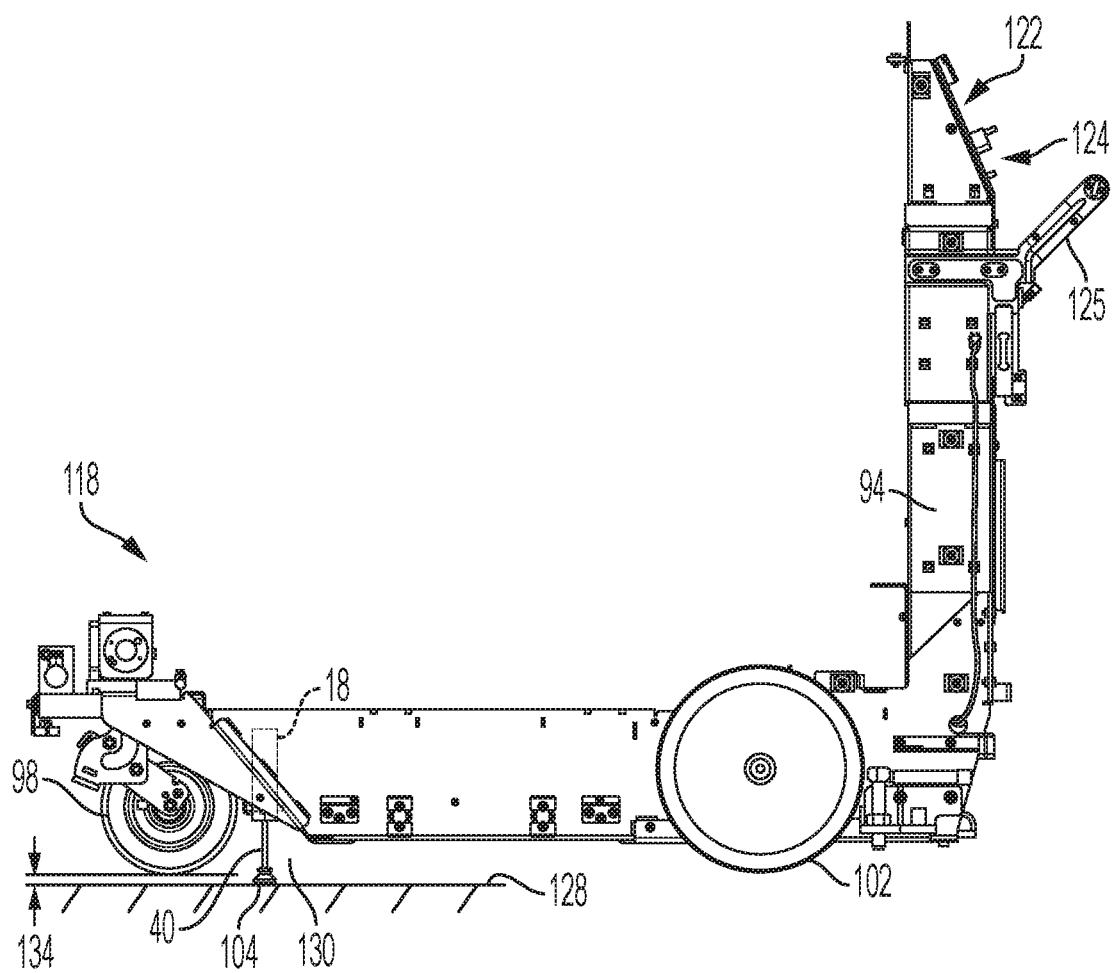

Referring to FIGS. 4A-4C, side views of the trolley 94 along view line 4-4 of FIG. 3A are shown. FIGS. 4A-4C depict downward movement of front stabilizing foot 104 (see FIG. 3A) from a retracted position 126 to a deployed position 130. The trolley 94 includes a receiving area 118 that receives the portable imaging system 82 and a handle 125 that may be used by an operator to facilitate maneuverability of the trolley 94. In addition, the trolley 94 includes a computer display 122 and controls 124 for controlling the portable imaging system 82 and the trolley 94. In particular, FIG. 4A schematically depicts, for example, front stabilizing foot 104 in the retracted position 126 wherein the front stabilizing foot 104 is spaced apart from a floor portion 128 by a first gap 132 and is not in contact with the floor portion 128.

Further, FIG. 4B depicts the front stabilizing foot 104 in the deployed position 130 wherein the front stabilizing foot 104 and front wheels 98 (see FIG. 3A) contact the floor portion 128. In the deployed position 130, the front stabilizing foot 104, connected to second shaft 40 (see FIG. 1), for example, extends downward from the second cylinder 18 such that the front stabilizing foot 104 contacts the floor portion 128 and sufficiently carries the load of the trolley 94 and portable imaging system 82 even though the wheels 98 touch the floor portion 128. In FIG. 4C, the front stabilizing foot 104 extends sufficiently downward from the second cylinder 18 such that wheels 98 are lifted above the floor portion 128 when the front stabilizing foot 104 contacts the floor portion 128 to form a second gap 134 between the wheels 98 and the floor portion 128. Thus, the load carried by the wheels 98 due to the trolley 94 and portable imaging system 82 is removed and transferred to the front stabilizing foot 104. In the configuration shown in FIG. 3B, for example, the load carried by the wheels 98 is removed and transferred to the first 108 and second 110 stabilizing feet when the first 108 and second 110 stabilizing feet contact the floor portion 128 and are in the deployed position 130, thus lifting the wheels 98 as previously described.

Figure 5A:
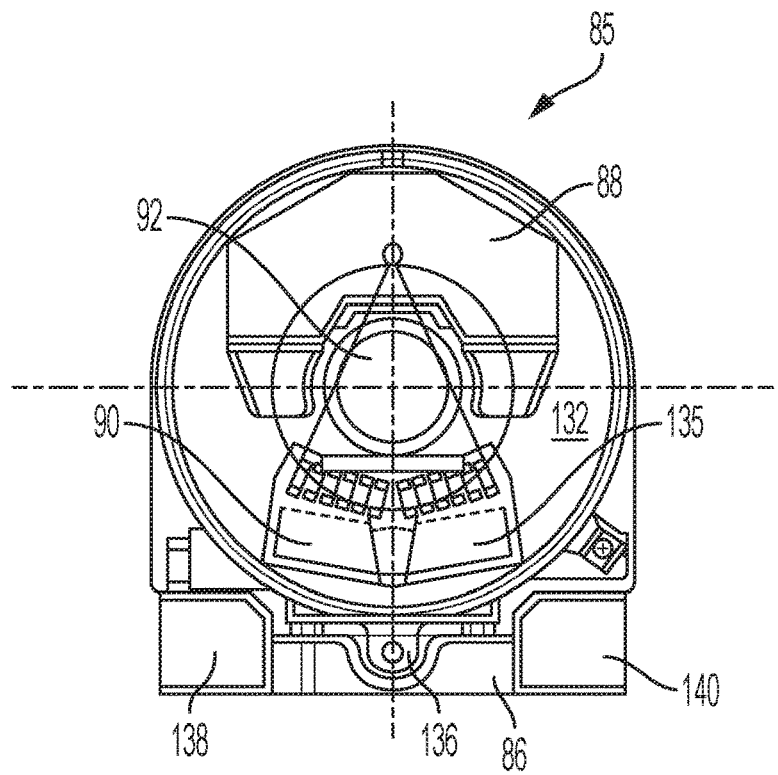
FIGS. 5A-5B depict more detailed schematic front and rear views, respectively, of a CT system for use in a first response vehicle.
Figure 5B:
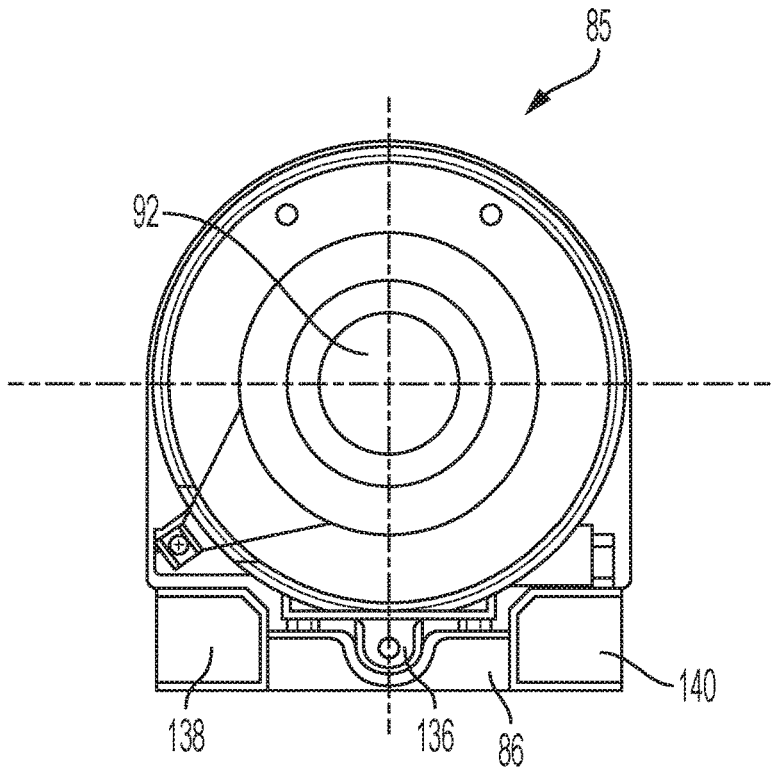

In accordance with aspects of the invention, the CT system 85 (FIG. 2) may be mounted directly to a first response vehicle 144 (see FIGS. 6A-6D) such as an ambulance without the use of a trolley 94 and associated stabilization feet 108, 110, 114, 116. FIGS. 5A-5B depict more detailed schematic front and rear views, respectively, of the CT system 85 for use in a first response vehicle 144. The CT system 85 includes a scanner component 132 in the form of a ring/doughnut assembly that comprises at least two major assemblies: a) the X-ray generator 88 (see FIG. 2), which includes an x-ray tube, high voltage power supply (HVPS), collimator, etc. and associated items and b) the X-ray detector assembly 90 (see FIG. 2) that includes a data acquisition system (DAS)/detector/control box 135 which includes detectors, spine, DAS, LVPS (low voltage power supply), interface electronics, data link electronics, etc. and associated items. The CT system 85 also includes an internal drive system 136 that translates the scanner component 132 (e.g., in one or more axes) relative to the base 86. The CT system 85 may further include a power distribution unit (PDU) assembly 138 that includes power electronics, batteries and associated components and an Electronic Control Unit (ECU) assembly 140 that includes the control, recon, interface electronics and associated items. The ECU assembly 140 may be operatively connected relative to a user interface (UI), and other control sub-systems. The ECU assembly 140 may also include a tethered/wired user interface control assembly for remote wired operation of the CT imaging system 85. The PDU assembly 138 may be advantageously configured to require a minimal external power supply connection prior to allowing for operation of the CT imaging system 85. Thus, e.g., while the CT imaging system 85 may include a battery back-up system for supplementing an irregular power supply, e.g., from a wall connection, a wired power supply connection may be required prior to operation of the device.

Figure 6A:
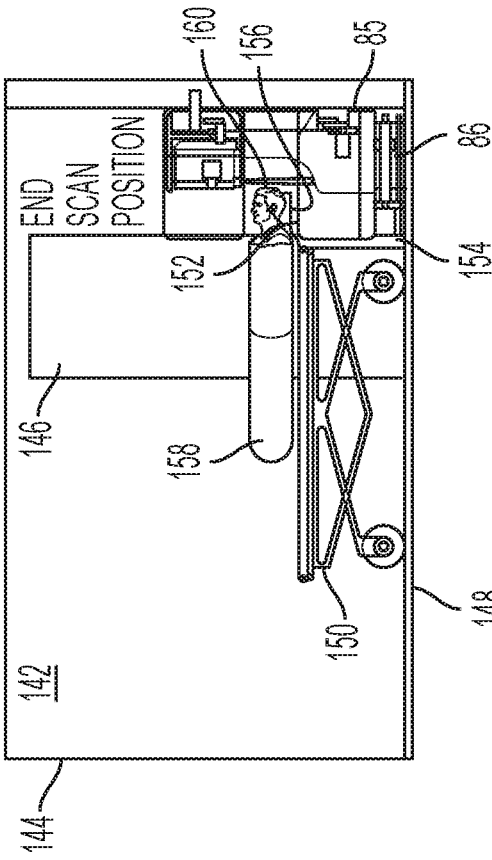
FIG. 6A depicts a patient transport position for a stretcher located in the first response vehicle.

Referring to FIGS. 6A-6D, the CT system 85 is shown located in an interior 142 of a first response vehicle 144 that is accessible, for example, via a side door 146. The base 86 of the CT system 85 described in relation to FIGS. 5A-5B is securely mounted directly to a structural floor and/or frame 148 of the first response vehicle 144 without the trolley 94 and associated stabilization feet 108, 110, 114, 116. Mounting the CT system 85 to the floor 148 of the first response vehicle 144 provides a lower center of gravity for the CT system 85 and ensures secure mounting during transport. Referring to FIG. 6A, a patient transport position is shown for a stretcher 150 located in the first response vehicle 144. In accordance with an aspect of the invention, the base 86 has a relatively low configuration to enable alignment with a relatively low patient platform such as stretcher 150 as typically employed in the first response vehicle 144 and to ensure a low center of gravity.

An integrated patient alignment mechanism 152 (or scan board) is attached to the CT system 85 by a post 154. The patient alignment mechanism 152 includes a head support 156 that is configured to align with the center opening 92 (see FIG. 5A) of the scanner component 132 of the CT system 85. The patient alignment mechanism 152 advantageously allows for proper alignment of a portion of the anatomy of a patient 158, such as the patient head 160, relative to the CT system 85 without requiring special adapters for an intensive care unit (ICU) bed, for example. In example embodiments, the patient alignment mechanism 152 serves as an interface between a patient support structure and the CT system 85.

Figure 6B:
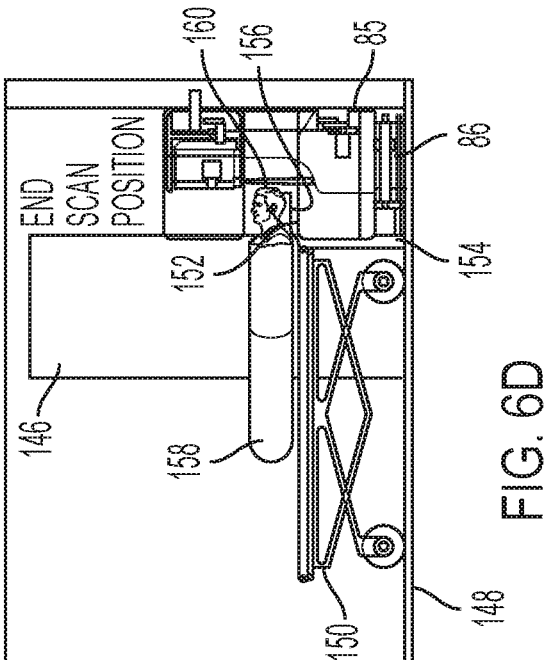
FIG. 6B depicts a scan position wherein the patient head is located on a head support.
Figure 6C:
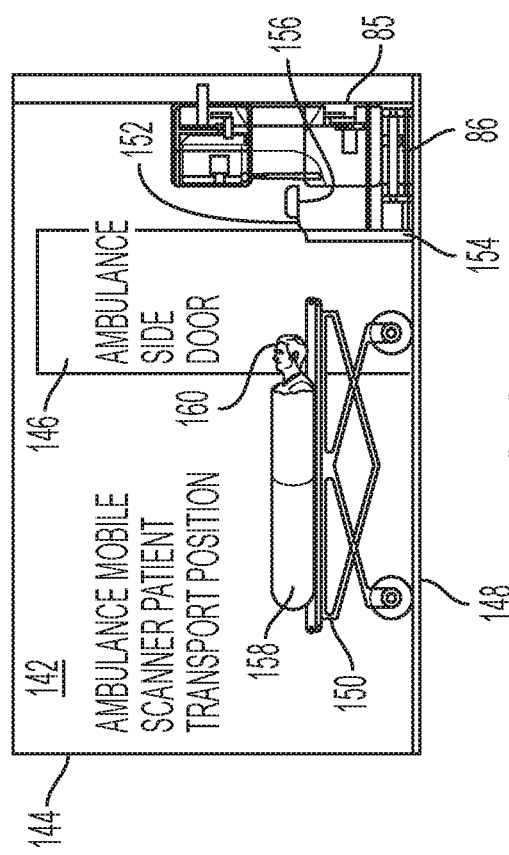
FIG. 6C depicts the scanner portion in a scanning position wherein the stationary patient head is received by a moving scanner portion that scans the patient head.
Figure 6D:
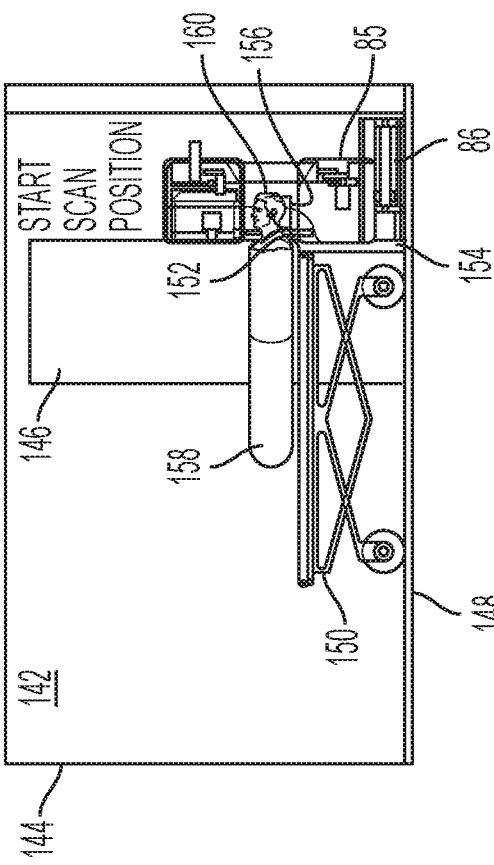
FIG. 6D depicts the scanner portion in an end scan position wherein the scanner portion is spaced apart from the patient head and scanning is stopped.

Referring to FIG. 6B, the patient 158 is moved on the stretcher 150 and onto the patient alignment mechanism 152 to a scan position wherein the patient head 160 is located on the head support 156 wherein the patient head 160 is stationary. In the scan position, the scanner portion 132 is spaced apart from the patient head 160 and is in a position ready for scanning the stationary patient head 160. For example, an ambulance or other mobile stretcher 150 may be positioned adjacent the patient alignment mechanism 152 and the height is adjusted to approximately correspond to the height of the patient alignment mechanism 152. The patient 158 is then moved to place the desired portion of the patient's anatomy, such as the patient head 160, on the patient alignment mechanism 152. It is important that the patient 158 (or portion of the patient's anatomy being scanned) is properly aligned in order to generate a suitable scan having reduced image noise and/or artifacts. The patient alignment mechanism 152 is secured relative to the base/platform 120 of the CT system 85. In accordance with an aspect of the invention, use of an integrated patient alignment mechanism 152 that is secured to the CT system 85 instead of a patient platform ensures greater reliability and improves the ease of use of the CT system 85 by negating the need for different adapters depending for different types of patient platforms. Referring to FIG. 6C, the scanner portion 132 is shown in a scanning position wherein the stationary patient head 160 is received by a moving scanner portion 132 that scans the patient head 160. Referring to FIG. 6D, the scanner portion 132 is shown in an end scan position wherein the scanner portion 132 is spaced apart from the patient head 160 and scanning is stopped.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A hydraulic stabilizer system for stabilizing a portable medical imaging system located on a trolley positioned on a floor having uneven floor portions, comprising:
- at least two hydraulic cylinders each having a shaft extending through a first wall of the respective cylinder, wherein each shaft is moveable relative to the respective cylinder and a second end of each shaft includes a stabilizing foot that contacts associated uneven floor portions;
- a spring support element located in each cylinder, wherein a first end of each shaft includes the spring support element;
- a retraction spring located between the spring support element and an inner surface of the first wall of each cylinder;
- a hydraulic circuit for supplying hydraulic fluid to the cylinders, wherein the cylinders are in fluid communication with each other; and
- a pump that pumps hydraulic fluid into the cylinders, wherein hydraulic pressure against the spring support elements causes downward movement of the shafts and associated feet until the feet contact the associated uneven floor portions such that the pressure exerted by the feet against the associated uneven floor portions is equalized thereby stabilizing the trolley and wherein the downward movement of the spring support elements compresses the retraction spring in each cylinder.

2. The stabilizer system according to claim 1, further including a retract valve located in the hydraulic circuit, wherein when the retract valve is opened hydraulic pressure in the cylinders is relieved to cause the retraction springs in each cylinder to expand and cause upward movement of the feet into a retracted position.

3. The stabilizer system according to claim 1, further including an extend valve to enable fluid communication between the pump and the cylinders.

4. The stabilizer system according to claim 1, further including a pressure switch wherein hydraulic fluid is pumped into the cylinders until a predetermined pressure is detected by the pressure switch.

5. The stabilizer system according to claim 1, wherein a stroke length of a foot is greater than a stroke length of another foot.

6. The stabilizer system according to claim 1, wherein the pressure exerted on the feet is sufficient to stabilize the portable imaging system without completely supporting the weight of the portable imaging system.

7. The stabilizer system according to claim 1, further including a pressure relief valve that limits the hydraulic pressure in the stabilizer system.

8. A hydraulic stabilizer system for stabilizing a portable medical imaging system located on a trolley positioned on a floor having uneven floor portions, comprising:
- first and second hydraulic cylinders having first and second shafts, respectively, extending through a first wall of the respective cylinder, wherein the first and second shafts are moveable relative to the first and second cylinders and a second end of the first and second shafts includes first and second stabilizing feet, respectively, that contact associated floor portions;
- first and second spring support elements located in the first and second cylinders, respectively, wherein a first end of the first and second shafts includes first and second spring support elements;
- first and second retraction springs located between the first and second spring support elements and an inner surface of the first wall of the first and second cylinders, respectively;
- a hydraulic circuit for supplying hydraulic fluid to the first and second cylinders, wherein the first and second cylinders are in fluid communication with each other;
- a pump that pumps hydraulic fluid to the first and second cylinders, wherein hydraulic pressure against the first and second spring support elements causes downward movement of the first and second shafts and first and second feet, respectively, until the first and second feet contact the associated uneven floor portions such that the pressure exerted by the first and second feet against the associated uneven floor portions is equalized thereby stabilizing the trolley and wherein the downward movement of the first and second spring support elements compresses the first and second retraction springs; and
- a retract valve located in the hydraulic circuit, wherein when the retract valve is opened hydraulic pressure in the first and second cylinders is relieved to cause the first and second retraction springs to expand and cause upward movement of the first and second feet into a retracted position.

9. The stabilizer system according to claim 8, further including a retract valve located in the hydraulic circuit, wherein when the retract valve is opened hydraulic pressure in the first and second cylinders is relieved to cause the first and second retraction springs in each cylinder to expand and cause upward movement of the first and second feet into a retracted position.

10. The stabilizer system according to claim 8, further including an extend valve to enable fluid communication between the pump and the first and second cylinders.

11. The stabilizer system according to claim 8, further including a pressure switch wherein hydraulic fluid is pumped into the first and second cylinders until a predetermined pressure is detected by the pressure switch.

12. The stabilizer system according to claim 8, wherein a stroke length of the first foot is greater than a stroke length of the second foot.

13. The stabilizer system according to claim 8, wherein the pressure exerted on the first and second feet is sufficient to stabilize the portable imaging system without completely supporting the portable imaging system.

14. The stabilizer system according to claim 8, further including a pressure relief valve that limits the hydraulic pressure in the stabilizer system.

15. The stabilizer system according to claim 8, wherein the trolley includes motorized wheels.

16. A method of stabilizing a portable medical imaging system located on a trolley positioned on a floor having uneven floor portions, comprising:
- providing at least two hydraulic cylinders each having a shaft extending through a first wall of the respective cylinder, wherein each shaft is moveable relative to the respective cylinder and a second end of each shaft includes a stabilizing foot that contacts associated uneven floor portions;
- providing a spring support element located in each cylinder, wherein a first end of each shaft includes the spring support element;

providing a retraction spring located between the spring support element and an inner surface of the first wall of each cylinder;

supplying hydraulic fluid to the cylinders, wherein the cylinders are in fluid communication with each other;

pumping hydraulic fluid into the cylinders, wherein hydraulic pressure against the spring support elements causes downward movement of the shafts and associated feet until the feet contact the associated uneven floor portions such that the pressure exerted by the feet against the associated uneven floor portions is equalized thereby stabilizing the trolley and wherein the downward movement of the spring support elements compresses the retraction spring in each cylinder.

17. The method according to claim 16, further including relieving hydraulic pressure in the cylinders to cause the retraction springs in each cylinder to expand and cause upward movement of the feet into a retracted position.

18. The method according to claim 16, further including providing an extend valve to enable fluid communication between the pump and the cylinders.

19. The method according to claim 16, wherein a stroke length of a foot is greater than a stroke length of another foot.

20. The method according to claim 16, further including exerting pressure on the feet that is sufficient to stabilize the portable imaging system without completely supporting the weight of the portable imaging system.

* * * * *